(12) United States Patent
Luly

(10) Patent No.: US 7,731,911 B2
(45) Date of Patent: Jun. 8, 2010

(54) FLUORINATION REACTOR

(75) Inventor: Matthew H. Luly, Hamburg, NY (US)

(73) Assignee: Honeywell International Inc., Morristown, NJ (US)

( * ) Notice: Subject to any disclaimer, the term of this patent is extended or adjusted under 35 U.S.C. 154(b) by 184 days.

(21) Appl. No.: 11/549,057

(22) Filed: Oct. 12, 2006

(65) Prior Publication Data

US 2007/0154368 A1 Jul. 5, 2007

Related U.S. Application Data

(62) Division of application No. 11/326,379, filed on Jan. 4, 2006, now Pat. No. 7,247,759.

(51) Int. Cl.
| | |
|---|---|
| B01J 10/00 | (2006.01) |
| B01J 12/00 | (2006.01) |
| B01J 15/00 | (2006.01) |
| B01J 19/00 | (2006.01) |
| C07C 17/38 | (2006.01) |

(52) U.S. Cl. .................. 422/129; 422/191; 570/179
(58) Field of Classification Search .................. 422/429, 422/191; 571/179
See application file for complete search history.

(56) References Cited

U.S. PATENT DOCUMENTS

| 4,377,715 A | 3/1983 | Nychka |
| 4,579,974 A * | 4/1986 | Cheminal et al. ............ 568/394 |
| 4,599,455 A * | 7/1986 | Maruyama et al. .......... 568/411 |
| 4,680,406 A * | 7/1987 | Fujioka ....................... 546/345 |
| 4,827,024 A * | 5/1989 | Guglielmo et al. .......... 560/300 |
| 4,859,747 A | 8/1989 | Bierschenk et al. |
| 5,675,046 A | 10/1997 | Ohno et al. |
| 5,739,070 A * | 4/1998 | Ebmeyer et al. .............. 502/37 |
| 6,395,940 B1 * | 5/2002 | Komata et al. .............. 570/160 |
| 2001/0034465 A1 * | 10/2001 | Swain et al. ................. 570/170 |
| 2002/0156321 A1 * | 10/2002 | Syvret ......................... 562/849 |
| 2005/0027132 A1 * | 2/2005 | Takagi et al. ................ 549/533 |

FOREIGN PATENT DOCUMENTS

DE 101 59 940 6/2003

OTHER PUBLICATIONS

Froning et al., Indus. Eng. Chem., 39(3), 275-278 (1947).
XP 002443109 & JP 02 117626 (Osaka Gas Co Ltd) May 2, 1990; Derwent Publicatins Ltd., Lond, GB; An 1990-181331.

* cited by examiner

Primary Examiner—Walter D Griffin
Assistant Examiner—Natasha Young
(74) Attorney, Agent, or Firm—Bruce Bradford

(57) ABSTRACT

A fluorination reactor having a reaction zone, an inlet for supplying an organic compound to be fluorinated to the reaction zone, an inlet for supplying elemental fluorine to the reaction zone, and an outlet for recovering a fluorinated reaction product, wherein the reaction zone includes a fluoride-adsorbing composition for adsorbing any HF produced as a byproduct of the reaction between the organic compound and elemental fluorine.

12 Claims, 6 Drawing Sheets

FLUORINATION REACTOR

CROSS-REFERENCE TO RELATED APPLICATION

The present application is a Divisional of U.S. application Ser. No. 11/326,379 filed Jan. 4, 2006, the disclosure of which is incorporated by reference.

BACKGROUND OF THE INVENTION

The present invention relates to improvements to fluorination reactions using elemental fluorine in which HF is formed as a byproduct. In particular, the present invention relates to fluorination reactions in which the reactants are contacted in the presence of an HF-adsorbing composition, so any HF formed is removed from the reaction system to prevent the formation of other undesirable hydrogen-containing byproducts. The present invention also relates to improved fluorination reactors with reaction zones packed with HF-adsorbing compositions.

BACKGROUND ART

Reactions of elemental fluorine ($F_2$) with many materials, especially organic compounds, can be quite exothermic and $CF_4$ is generally the thermodynamically preferred reaction product. Various reactor designs have been proposed to control such reactions and allow the fluorination to be halted short of producing high yields of $CF_4$. For example, U.S. Pat. No. 4,377,715 describes the use of porous tube reactors to contact fluorine and organics in a controlled fashion. U.S. Pat. No. 5,675,046 describes the use of a two reaction zone system to produce perfluorocarbons. Such reactors are designed to control the reaction. They are also generally designed to minimize the formation of thermodynamically favored $CF_4$.

FIG. 1 shows the calculated thermodynamic equilibrium as a function of temperature for the reaction $C_2HF_5+F_2=C_2F_6+HF$ based on the initial composition of one mole of $C_2HF_5$ and one mole of $F_2$. FIG. 1 shows that for all practical purposes thermodynamics predicts the reaction is quantitative with 1 mole of $C_2HF_5$ and 1 mole of $F_2$ yielding essentially 1 mole of $C_2F_6$ and one mole of HF. FIG. 1 shows the amount of unreacted $F_2$ and $C_2HF_5$ will be less than about $10^{-10}$ moles over the temperature range 0 to about 500 C.

Thermodynamic calculations are very useful for predicting if a given reaction will occur and what the maximum yield will be. However, it is not always possible to achieve the predicted results in the laboratory. One reason is thermodynamics gives no indication how long it may take for reaction to reach equilibrium. Another reason is if a stable compound is omitted from the calculation, an erroneous result may be obtained.

For example, when $C_2HF_5$ and $F_2$ are reacted in the laboratory, some $CF_4$ and $CH_3F$ are observed as co-products. FIG. 3 shows the calculated thermodynamic equilibrium as a function of temperature for the reaction $C_2HF_5+F_2=C_2F_6+HF+CF_4+CHF_3$ based on the initial composition of one mole of $C_2HF_5$ and one mole of $F_2$. FIG. 3 shows that $CF_4$ is the thermodynamically favored product over the temperature range studied, but the amount produced should decrease as the temperature increases. $CF_4$ dominates the products because of its extreme stability. The fact that the reaction of $C_2HF_5$ with $F_2$ produces significant quantities of $C_2F_6$, in contrast to the calculated thermodynamic equilibrium shows kinetic factors come into play and the laboratory reaction does not reach thermodynamic equilibrium.

Metal fluorides have long been used to absorb HF. For example, Froning, et al., *Indus. Eng. Chem.*, 39(3), 275 (1947) describe the use of sodium fluoride pellets to remove HF from fluorine. The paper shows that the vapor pressure of HF over $NaHF_2$ increases as temperature increases until at about 278 C, the vapor pressure of HF is 1 atm. Therefore at temperatures greater than 278 C, sodium fluoride/bifluoride is not effective at removing HF from a gas stream. Sodium fluoride has also been used to scrub HF from a reactor effluent prior to analysis in order to simplify collection of product and subsequent analysis as in U.S. Pat. No. 4,377,715.

U.S. Pat. No. 4,859,747 describes the use of sodium fluoride in the direct fluorination of solid and liquid ethers allowing the use of more severe fluorination conditions (higher fluorine concentration and faster rates of fluorine delivery). In this patent the sodium fluoride is disclosed to scavenge HF and prevent reaction of the HF with the oxygen linkages of the ether. It is quite specific for this ether application and discloses using stoichiometric amounts of the sodium fluoride, running the reaction in a batch mode, and the importance of keeping the starting material from being swept out of the reactor before fluorination is complete. However, the use of metal fluorides to control the thermodynamically dictated distribution of reaction products is not known.

SUMMARY OF THE INVENTION

It has now been discovered that packing a fluorination reactor with a fluoride-adsorbent such as sodium fluoride will increase the yield in reactions where hydrogen-containing byproducts are possible. Removing HF from the reaction prevents the HF from reacting with the compound to be fluorinated to form unwanted hydrogen-containing byproducts.

Therefore, according to one aspect of the present invention, a fluorination reaction is provided in which an organic compound to be fluorinated is contacted with elemental fluorine and HF is produced as a byproduct, wherein the elemental fluorine is contacted with the organic compound in the presence of a fluoride-adsorbing composition so that the amount of HF or another hydrogen-containing byproduct is reduced or eliminated. According to one embodiment of this aspect of the invention, the organic compound is a fluorohydrocarbon.

Another embodiment of this aspect of the invention is a reaction in which the fluoride-adsorbing composition contains one or more compounds selected from alkali metal halides and alkaline earth halides and fluoride-adsorbing polymers. In a preferred embodiment, the fluoride-adsorbing composition contains sodium fluoride.

The fluorination reaction of the present invention is implemented by packing the reaction zone of a fluorination reactor with the fluoride-adsorbing composition. Therefore, according to another aspect of the present invention, a fluorination reactor is provided having a reaction zone, an inlet for supplying an organic compound to be fluorinated to the reaction zone, an inlet for supplying elemental fluorine to the reaction zone to react with and fluorin-ate the organic compound, and an outlet for recovering a fluorinated reaction product, where the reaction zone contains an fluoride-adsorbing composition for removing any HF produced as a byproduct of the reaction between the organic compound and the elemental fluorine.

According to one embodiment of this aspect of the invention, the reactor is a vapor phase reactor and the fluoride-adsorbing composition is a solid-phase material. According to another embodiment of this aspect of the invention, means are provided for replenishing the fluoride-adsorbing composition. According to a preferred embodiment the replenishment means includes means for heating the fluoride-adsorbing composition so that the HF is de-sorbed and an inlet for supplying an inert gas flow so that the desorbed HF is swept from the reactor through an outlet.

The foregoing and other objects, features and advantages of the present invention are more readily apparent from the detailed description of the preferred embodiments set forth below, taken in conjunction with the accompanying drawings.

DETAILED DESCRIPTION OF PREFERRED EMBODIMENTS

Figure 1:
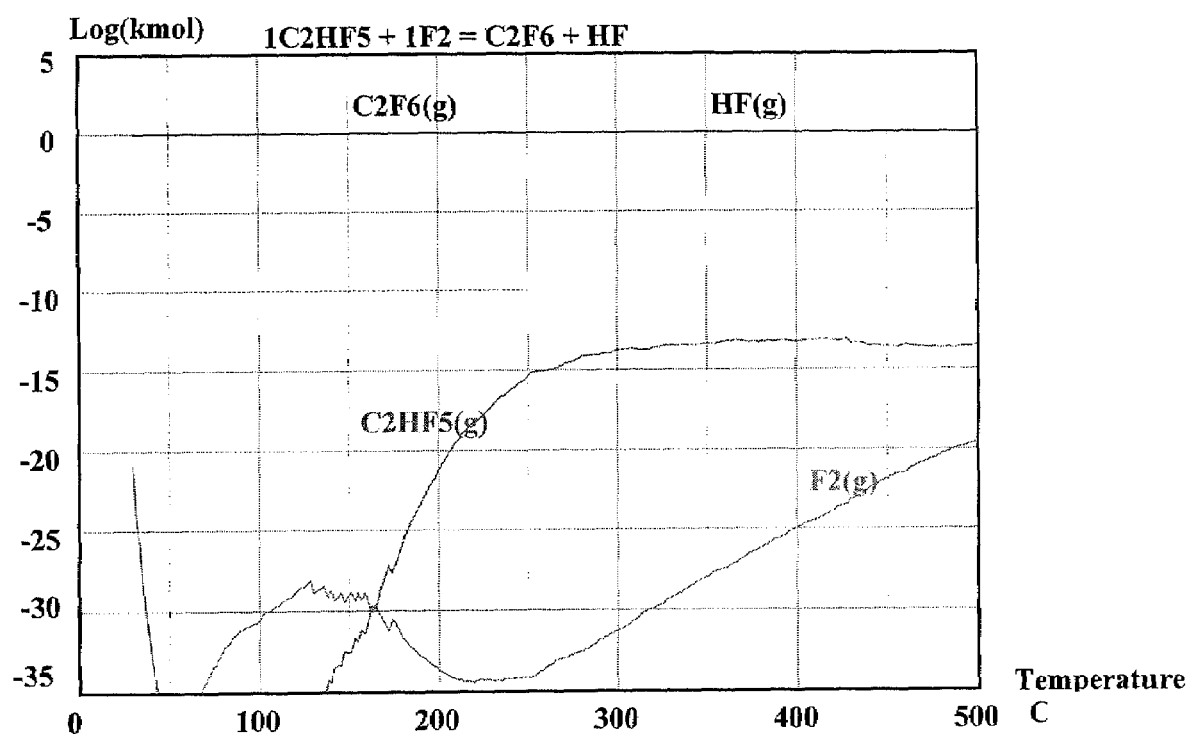
FIG. 1 shows the calculated thermodynamic equilibrium as a function of temperature for the reaction $C_2HF_5+F_2=C_2F_6+HF$ based on the initial composition of one mole of $C_2HF_5$ and one mole of $F_2$.
Figure 2:
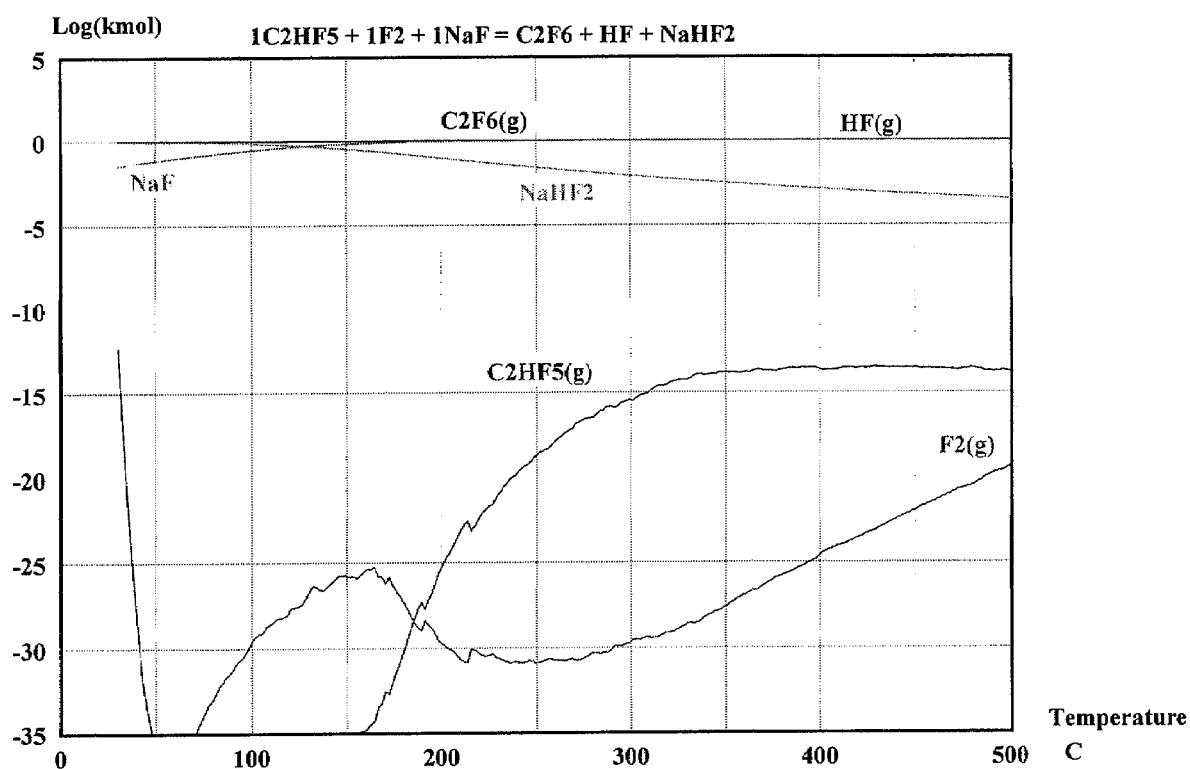
FIG. 2 shows the calculated thermodynamic equilibrium as a function of temperature for the reaction $C_2HF_5+F_2+NaF=C_2F_6+HF+NaHF_2$ based on the initial composition of one mole of $C_2HF_5$, one mole of $F_2$ and mole of $NaHF_2$.
Figure 3:
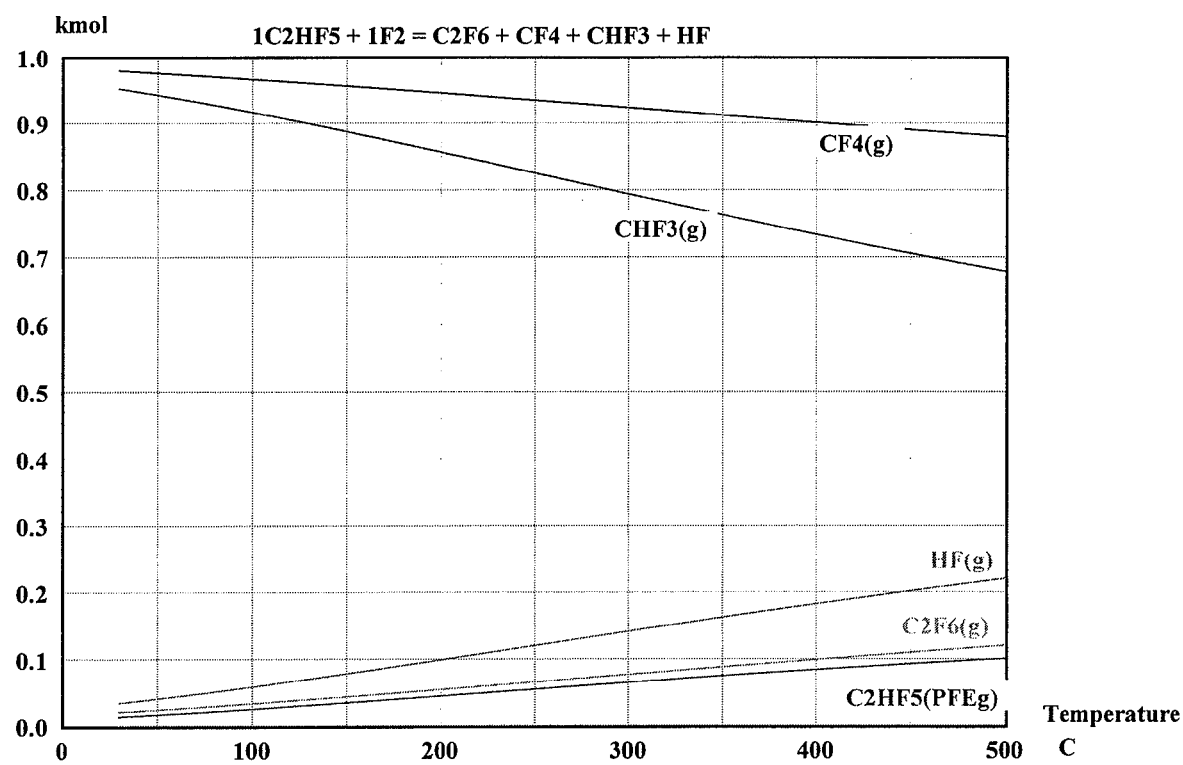
FIG. 3 shows the calculated thermodynamic equilibrium as a function of temperature for the reaction $C_2HF_5+F_2=C_2F_6+HF+CF_4+CHF_3$ based on the initial composition of one mole of $C_2HF_5$ and one mole of $F_2$.
Figure 4:
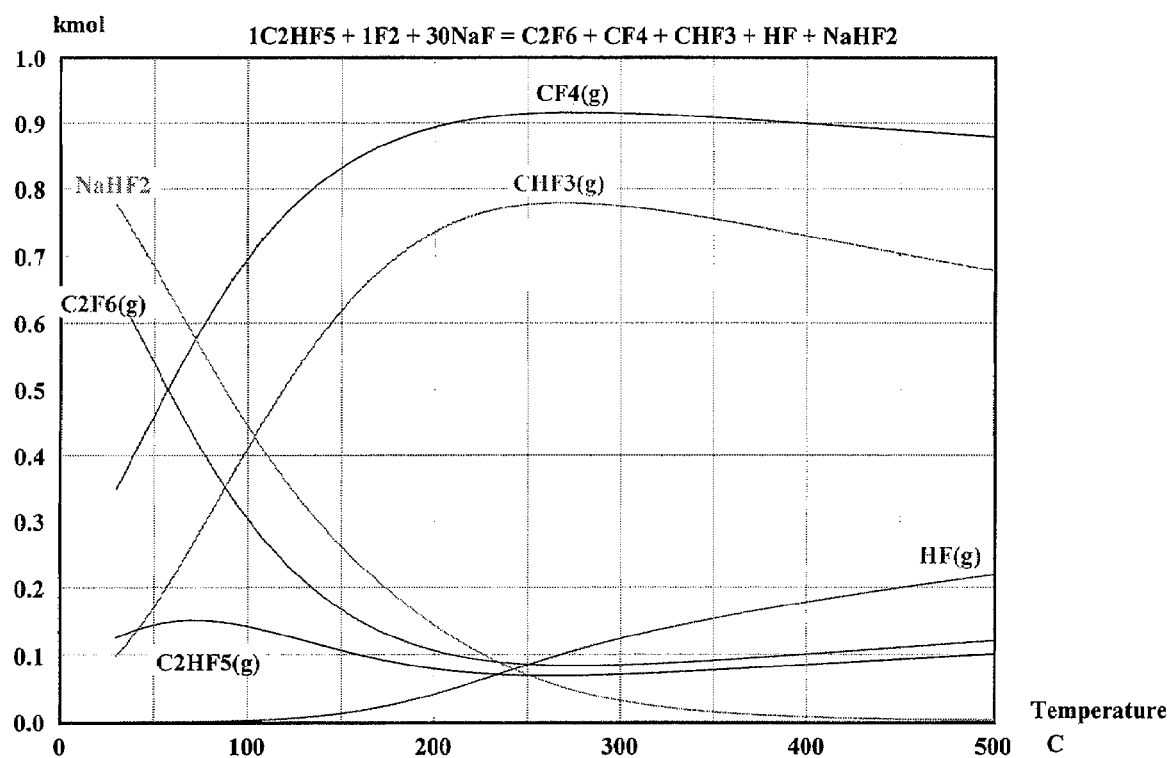
FIG. 4 shows how the addition of sodium fluoride changes the equilibrium of the reaction of FIG. 3.

FIG. 4 shows how the addition of sodium fluoride changes the equilibrium of the reaction of FIG. 3:

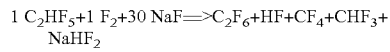

Figure 5:
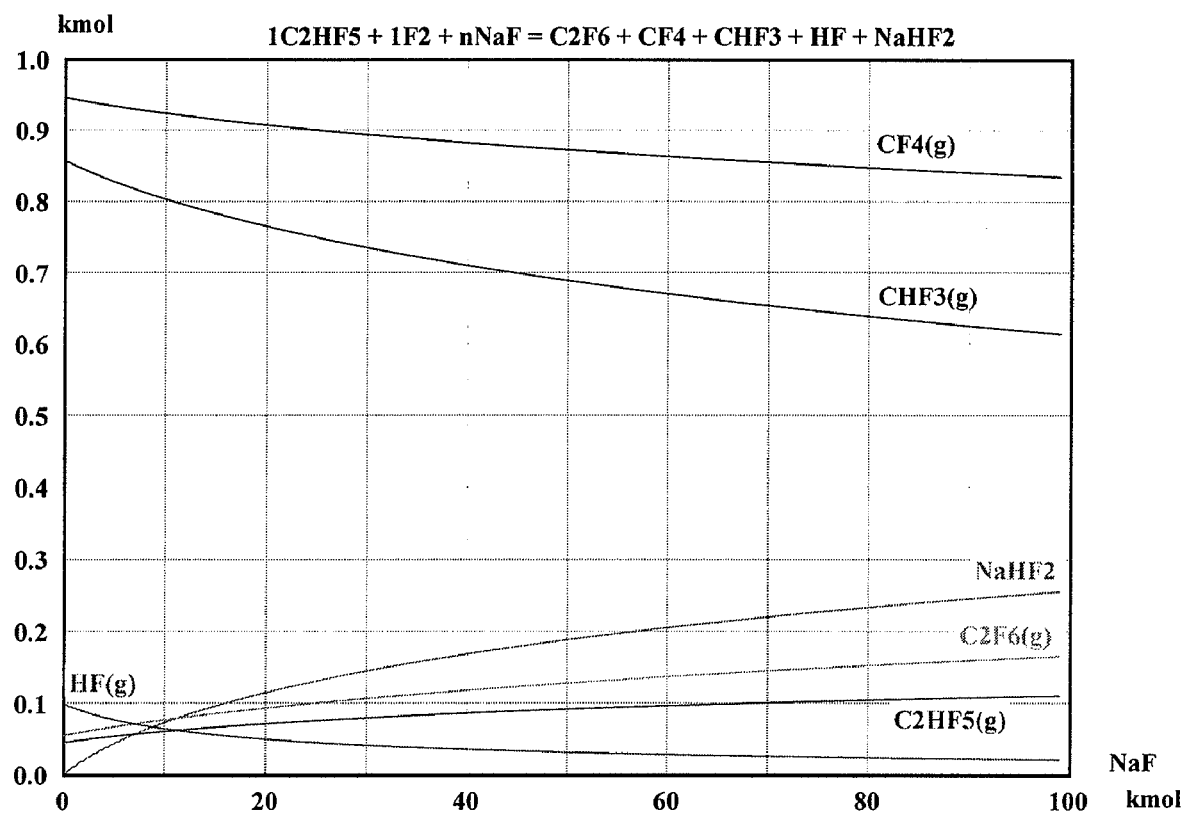
FIG. 5 shows how the equilibrium of the reaction of FIG. 4 varies as the amount of NaF changes at 100 C for the same reaction.

For example, at 100 C (no NaF) less than 0.05 kmole of $C_2F_6$ are formed, while under identical conditions with 30 kmole of NaF initially present, about 0.3 kmole of $C_2F_6$ is formed. FIG. 5 shows how the equilibrium composition varies as the amount of NaF changes at 100 C for the same reaction, and that above about 280 C, there is no difference between FIG. 3 and FIG. 4, i.e., the $NaF/NaHF_2$ ratio has no effect on the equilibrium. By removing HF from the vapor stream, hydrogen containing byproducts are less likely to form. This is clearly shown in how FIG. 4 differs from FIG. 3 at temperatures below about 280 C.

This has practical implications for vapor and liquid phase fluorinations, and can be implemented in various ways. The reaction zone or zones of a fluorination reactor are packed with a stoichiometric excess of a fluoride-adsorbing composition relative to the molar quantities of organic compound to be fluorinated and the elemental fluorine to be used. The stoichiometric excess may partially or completely fill each reaction zone. The adsorbent composition, when in the solid phase should have a particle size selected to maximize the surface area available for contact with the reaction mixture without significantly impeding the flow of the reactants and reaction products through each reaction zone. The largest practical quantity of adsorbent composition is preferred, because this will reduce the frequency at which the adsorbent composition must be replaced and/or regenerated. These parameters can be readily determined by one of ordinary skill in the art without undue experimentation.

A single reactor can be used. When an increase in HF or other hydrogen containing byproduct is detected, the feeds can be stopped and, for example, when the adsorbent composition contains sodium fluoride, the sodium fluoride/sodium bifluoride mixture can be replaced or regenerated. Or, two or more reactors in parallel can be employed so that when an increase in HF or other hydrogen containing byproduct is detected, the feeds are switched to another reactor containing fresh sodium fluoride while the spent sodium fluoride/sodium bifluoride mixture in the first reactor is regenerated.

Detection means include a sample collection means in communication with the reactor outlet, such as a splitter, which is in turn in communication with a separation means, such as a gas chromatograph, that in turn is in communication with a means for identifying the separated fractions, typically a spectrophotometric device such as a mass spectrophotometer or an infra-red spectrophotometer. The separation means preferably quantitatively determines the amount of each fraction present. Depending on the exact chemistry, it may not be necessary to use a split the material into fractions. For example, some mixtures can be directly analyzed by infrared spectroscopy. Also, different reactions might require different analytical techniques. GC or IR alone might be sufficient in some cases, while GC-MS might be required in other cases. This can be readily determined by one of ordinary skill in the aart without undue experimentation. The reactor or reactors can also include means for separating and returning non-reacted quantities of the organic compound and elemental fluorine to their respective reactor inlets.

Other reactor designs are also possible wherein a portion of an adsorbent composition such as sodium fluoride/sodium bifluoride is removed periodically or continuously and replaced with fresh material. Full regeneration of an adsorbent such as sodium fluoride or sodium bifluoride is performed by heating the mixture at about or above 280 C, and preferably between about 280 C and about 300 C under a flow of inert gas to de-sorb HF, which is swept out by the inert gas, to re-form NaF. While a full regeneration at 280-300 C is preferred, it is be possible to do a partial regeneration at a lower temperature. In addition to sodium fluoride, other solid fluoride absorbers may also be used, examples of which include alkalai metal halides, alkalai earth halides, and the like.

Organic compounds that may be fluorinated by the method of the present invention include hydrocarbons and halohydrocarbons containing the same or different halogen atoms selected from fluorine, chorine, bromine and iodine. The inventive method is exemplified using fluorohydrocarbons. The organic comounds may be aliphatic or aromatic. Aliphatic organic compounds may be saturated or unsaturated and straight chained or branched. The aliphatic and aromatic compounds may be substitued with one or more non-halogen substituents that are inert to elemental fluorine under fluorination reaction conditions, or are selected to react with elemental fluorine to produce a predetermined reaction product.

Figure 6:
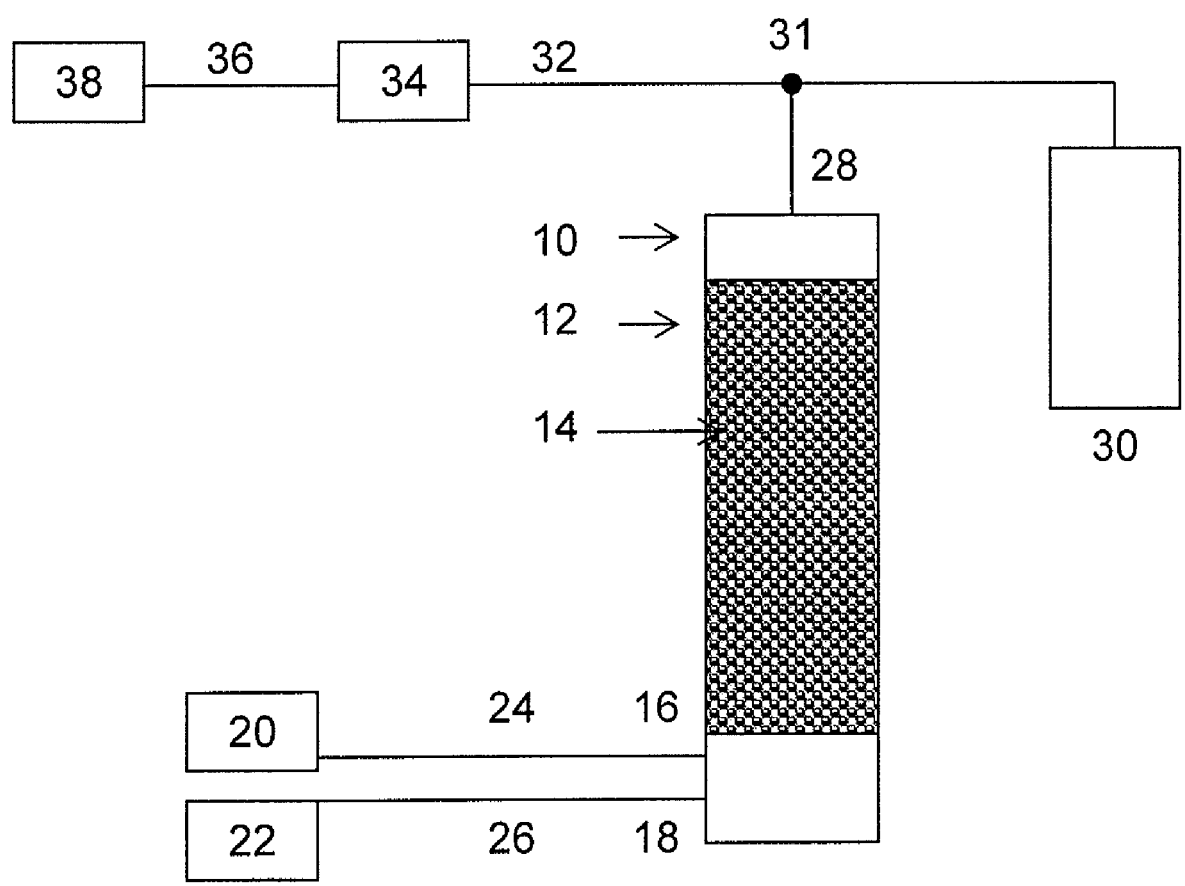
FIG. 6 depicts a fluorination reactor according to one embodiment of the present invention.

A fluorination reactor according to the present invetion is depicted in FIG. 6. Reactor 10 has reaction zone 12 packed with particles 14 of a fluoride-adsorbing composition. Depicted in this embodiment is sodium fluoride. Respective first and second reagent inlets 16 and 18 respectively deliver elemental fluorine and the organic compound to be fluorinated to the reaction zone 12 from respective storage vessels 20 and 22 through lines 24 and 26. The reaction product or products then exit through outlet 28 to collection vessel 30, after first passing through a scrubber means for the removal of undesirable materials such as excess $F_2$ (not shown). The collection vessel 30 depicted in this embodiment is a chilled cylinder While this shows the fundamental concept, variations are possible. For example, the feed materials might be pre-heated. Or, the feed materials might be pre-mixed. Or the $F_2$ might be introduced at multiple points to keep local $F_2$ concentrations low. These and other possibilities described for prior art fluorination reactors are compatible and may be employed with the HF adsorbing reactor described here.

Splitter 31 at outlet 28 samples the reaction product products, which are then delivered by line 32 to gas chromatograph 34, where the sample is quantitatively fractionated. Each fraction is then delivered by line 36 to an infra-red spectrophotometer 38, where each fraction is identified. Other detector means may be employed with, or as an alternative to, the infrared spectrophotometer, as previously discussed. As hydrogen-containing byproducts are detected a determination is made whether to replace and/or regenerate the adsorbent composition.

A plurality of reaction products, if obtained, can be separated by conventional means for recovery of the desired product, re-use of non-reacted starting materials and re-working of undesired byproducts. The isolation of the components of the reaction product is well understood by those of ordinary skill in the art.

The present invention thus provides a means by which organic compounds may be more efficiently fluorinated. The following non-limiting examples set forth hereinbelow illustrate certain aspects of the invention. All parts and percentages are by weight unless otherwise noted and all temperatures are in degrees Celsius.

EXAMPLES

Example 1

Fluorine diluted with nitrogen (about 18% $F_2$ in $N_2$) was introduced into the bottom of a 24"×2" tubular reactor through a fritted disk welded into the tube. $C_2HF_5$ was introduced about 2 inches above the fluorine inlet at a $C_2HF_5$ to $F_2$ ratio of about 1:1. The reaction zone temperature was 230 C. The crude product gas was passed sequentially through 10% aqueous KOH, 10% aqueous KI, anhydrous alumina and anhydrous calcium sulfate scrubbers and then condensed in a chilled cylinder. Based on gas chromatographic analysis of the collected product, conversion of $C_2HF_5$ was 90%, selectivity for $C_2F_6$ was 98%, and selectivity for $CF_4$ was about 1.5%.

Example 2

The reactor in Example 1 is filled with ⅛ inch sodium bifluoride pellets, heated to about 300 C, and swept with nitrogen gas until no HF was detected in the exit stream. The reactor is then cooled to 230 C and Example 1 is repeated. The amount of $CF_4$ is significantly reduced.

Example 3

When the sodium bifluoride pellets in Example 2 become saturated with HF, the $F_2$ and organic flows are stopped. The temperature is increased to 300 C and the reactor is swept with nitrogen until no HF is detected in the exit stream. The reactor is then cooled to 230 C and Example 1 is repeated. Essentially identical results to Example 2 are obtained.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

What is claimed is:

1. A first fluorination reactor comprising a reaction zone, an inlet for supplying an organic compound to be fluorinated to said reaction zone, an inlet for supplying elemental fluorine to said reaction zone, and an outlet for recovering a fluorinated reaction product, wherein said reaction zone comprises a fluoride-adsorbing composition and said reaction zone is configured so that said elemental fluorine contacts said organic compound in the presence of said fluoride-adsorbing composition and the amount of HF or another hydrogen-containing product produced as a byproduct of the reaction between said organic compound and said elemental fluorine is thereby reduced or eliminated, and wherein the distribution of reaction products is changed as a result of the reduction or elimination of the HF or another hydrogen-containing product; and a means for replenishing said fluoride-adsorbing composition, said means comprising: (a) a supply of an organic compound and a supply of elemental fluorine in communication with the respective inlets of said first reactor: (b) a second fluorination reactor comprising a reaction zone containing a fluoride-adsorbing composition essentially free of HF and respective inlets for supplying an organic compound to be fluorinated and elemental fluorine to said reaction zone of said second fluorination reactor; and (c) a means for switching said supply of said organic compound and said supply of elemental fluorine from said respective inlets of said first reactor to said respective inlets of said second reactor.

2. The fluorination reactor of claim 1, wherein said reactor is a vapor phase reactor and said fluoride-adsorbing composition is a solid-phase material.

3. The fluorination reactor of claim 1, further comprising a means for detecting HF or another hydrogen-containing byproduct in said reaction product outlet.

4. The fluorination reactor of claim 1, wherein said replenishing means comprises means for discontinuing the supply of said organic compound, means for discontinuing the supply of elemental fluorine, means for heating said fluoride-adsorbing composition so that HF is de-adsorbed, an inlet for supplying an inert gas flow and an outlet for directing said flow from said reactor so that said de-adsorbed HF is swept from said reactor.

5. The fluorination reactor of claim 1, wherein said fluoride-adsorbing composition comprises a compound selected from the group consisting of alkali-metal halides and alkaline earth halides.

6. The fluorination reactor of claim 5, wherein said fluoride-adsorbing composition comprises sodium fluoride.

7. A system, comprising:
a first fluorination reactor comprising: a reaction zone; an inlet for supplying an organic compound to be fluorinated to said reaction zone; an inlet for supplying elemental fluorine to said reaction zone; and an outlet for recovering a fluorinated reaction product, wherein said reaction zone comprises a fluoride-adsorbing composition for adsorbing any HF or other hydrogen-containing products produced as a byproduct of the reaction between said organic compound and said elemental fluorine; and a means for replenishing said fluoride-adsorbing composition, said means comprising: (a) a supply of an organic compound and a supply of elemental fluorine in communication with the respective inlets of said first fluorination reactor; (b) a second fluorination reactor comprising a reaction zone containing a fluoride-adsorbing composition essentially free of HF and respective inlets for supplying an organic compound to be fluorinated and elemental fluorine to said reaction zone of said second reactor; and (c) a means for switching said supply of said organic compound and said supply of elemental fluorine from said respective inlets of said first reactor to said respective inlets of said second reactor.

8. The fluorination reactor of claim 7, wherein said reactor is a vapor phase reactor and said fluoride-adsorbing composition is a solid-phase material.

9. The fluorination reactor of claim 7, further comprising a means for detecting HF or another hydrogen-containing byproduct in said reaction product outlet.

10. The fluorination reactor of claim 7, wherein said replenishing means comprises means for discontinuing the supply of said organic compound, means for discontinuing the supply of elemental fluorine, means for heating said fluoride-adsorbing composition so that HF is de-adsorbed, an inlet for supplying an inert gas flow and an outlet for directing said flow from said reactor so that said de-adsorbed HF is swept from said reactor.

11. The fluorination reactor of claim 7, wherein said fluoride-adsorbing composition comprises a compound selected from the group consisting of alkali-metal halides and alkaline earth halides.

12. The fluorination reactor of claim 11, wherein said fluoride-adsorbing composition comprises sodium fluoride.

* * * * *